US010894105B2

(12) United States Patent
Erickson

(10) Patent No.: US 10,894,105 B2
(45) **Date of Patent: *Jan. 19, 2021**

(54) AIR POLLUTION ABATEMENT AND CROP GROWTH STIMULATION TECHNOLOGY

(71) Applicant: The Agricultural Gas Company, Inc., Petaluma, CA (US)

(72) Inventor: Stewart E. Erickson, Hudson, WI (US)

(73) Assignee: The Agricultural Gas Co., Petaluma, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 16/026,390

(22) Filed: Jul. 3, 2018

(65) Prior Publication Data

US 2019/0240364 A1 Aug. 8, 2019

Related U.S. Application Data

(60) Provisional application No. 62/528,189, filed on Jul. 3, 2017.

(51) Int. Cl.

| | |
|---|---|
| *A61L 2/20* | (2006.01) |
| *A01G 7/00* | (2006.01) |
| *C25B 1/12* | (2006.01) |
| *C25B 15/02* | (2006.01) |
| *A01G 13/00* | (2006.01) |
| *B01D 53/26* | (2006.01) |
| *A61K 39/395* | (2006.01) |
| *A61K 39/39* | (2006.01) |
| *A61K 39/08* | (2006.01) |
| *C07K 16/28* | (2006.01) |
| *A61K 39/00* | (2006.01) |

(52) U.S. Cl.

CPC ................ *A61L 2/20* (2013.01); *A01G 13/00* (2013.01); *A61K 39/08* (2013.01); *A61K 39/39* (2013.01); *A61K 39/395* (2013.01); *B01D 53/26* (2013.01); *C07K 16/2818* (2013.01); *C07K 16/2878* (2013.01); *C25B 1/12* (2013.01); *C25B 15/02* (2013.01); *A61K 2039/505* (2013.01); *A61K 2039/507* (2013.01); *A61K 2039/545* (2013.01); *A61K 2039/585* (2013.01); *A61K 2039/80* (2018.08); *B01D 2251/102* (2013.01); *B01D 2251/202* (2013.01)

(58) Field of Classification Search
CPC .............. A01G 7/00; A01G 13/00; A61L 2/20
See application file for complete search history.

(56) References Cited

U.S. PATENT DOCUMENTS

| | | | | |
|---|---|---|---|---|
| 4,744,951 | A * | 5/1988 | Cummings | A61L 2/20<br>422/27 |
| 2008/0264140 | A1 * | 10/2008 | Hill | G01N 33/0006<br>73/1.03 |
| 2016/0257055 | A1 * | 9/2016 | Hayakawa | B29C 49/46 |

* cited by examiner

*Primary Examiner* — Monica L Barlow
(74) *Attorney, Agent, or Firm* — Joel Skinner; Skinner & Associates

(57) ABSTRACT

A system and method of abating air pollution and stimulating crop growth. A reagent is introduced to a crop canopy to neutralize air pollutants within said canopy, wherein the reagent induces an oxidation-reduction chemical reaction with the air pollution present throughout the acreage of crops, and by means of the reaction effectually neutralizes the harmful effects of the air pollutants on the crops. The reagent is diluted using a venturi valve or other means. The flow rate of said reagent is regulated using an electronic control unit, based on data collected from at least one type of sensor in the canopy that is in communication with the control unit.

15 Claims, 1 Drawing Sheet

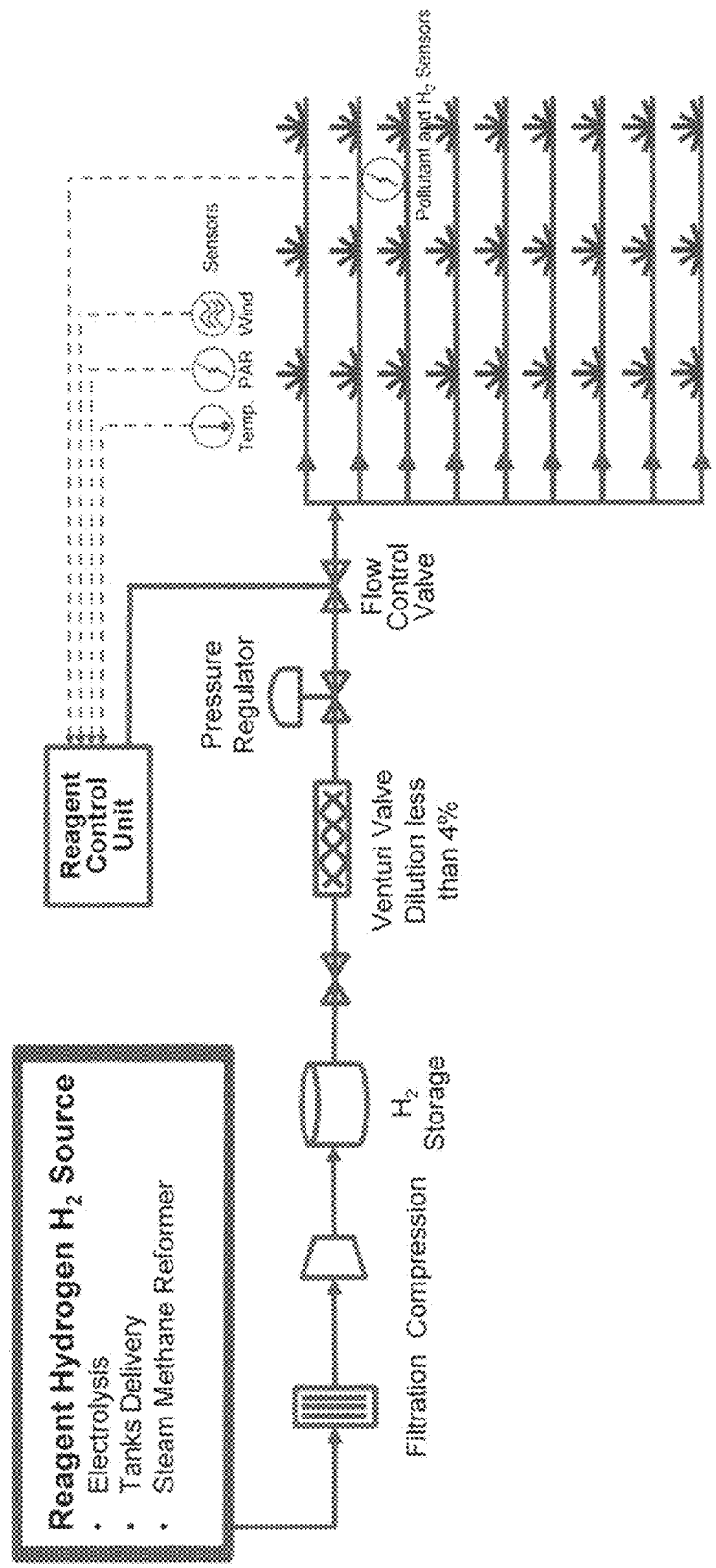

AIR POLLUTION ABATEMENT AND CROP GROWTH STIMULATION TECHNOLOGY

CROSS-REFERENCE TO RELATED APPLICATIONS, IF ANY

This application claims the benefit under 35 U.S.C. § 119(e) of U.S. Provisional Patent Application Ser. No. 62/528,189, filed Jul. 3, 2017, which is hereby incorporated by reference.

37 C.F.R. 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

BACKGROUND OF THE INVENTION

1. Field of the Invention

The present invention relates, generally, to agricultural and environmental systems, apparatus and methods. Particularly, the invention relates to a method of abating air pollution and stimulating crop growth.

2. Background Information

It may be hard to imagine that pollution could be invisible, but ozone is. The most widespread pollutant in the U.S. is also one of the most dangerous. Scientists have studied the effects of ozone on health for decades. Hundreds of research studies have confirmed that ozone harms people at levels currently found in the United States.

Ozone is also harmful to the plants we grow for nutrition. According to the United States Department of Agriculture, ground-level ozone causes more damage to plants than all other air pollutants combined. As a strong oxidant, ozone causes several types of symptoms including chlorosis and necrosis. Furthermore, controlled studies in open-top field chambers have repeatedly verified that flecking, stippling, bronzing and reddening on plant leaves are classical responses to ambient levels of ozone. In terms of crop yield loss caused by ozone, similar open-top studies conducted by the National Crop Loss Assessment Network showed between 35 and 45 percent yield loss among dicot species when exposed to ambient ozone at 100 parts per billion. The present invention hopes to ameliorate this situation.

What is Ozone?

Ozone (O3) is a gas molecule composed of three oxygen atoms. Often called "smog." ozone is harmful to breathe. Ozone aggressively attacks lung tissue by reacting chemically with it.

The ozone layer found high in the upper atmosphere (the stratosphere) shields us from much of the sun's ultraviolet radiation. However, ozone air pollution at ground level where we can breathe it (in the troposphere) causes serious health problems.

Where does Ozone Come From?

Ozone develops in the atmosphere from gases that come out of tailpipes, smokestacks and many other sources. When these gases come in contact with sunlight, they react and form ozone smog.

The essential raw ingredients for ozone come from nitrogen oxides (NOx), hydrocarbons, also called volatile organic compounds (VOCs) and carbon monoxide (CO). They are produced primarily when fossil fuels like gasoline, oil or coal are burned or when some chemicals, like solvents, evaporate. NOx is emitted from power plants, motor vehicles and other sources of high-heat combustion. VOCs are emitted from motor vehicles, chemical plants, refineries, factories, gas stations, paint and other sources. CO is also primarily emitted from motor vehicles.

If the ingredients are present under the right conditions, they react to from ozone. And because the reaction takes place in the atmosphere, the ozone often shows up downwind of the sources of the original gases. In addition, winds can carry ozone far from where it began.

Hydrogen as a Solution

For over 40 years, industry has used hydrogen in vast quantities as an industrial chemical and fuel for space exploration. During that time, industry has developed an infrastructure to produce, store, transport and utilize hydrogen safely.

Hydrogen is no more dangerous than other flammable fuels, including gasoline and natural gas. In fact, some of hydrogen's differences actually provide safety benefits compared to gasoline or other fuels. However, all flammable fuels must be handled responsibly.

Like gasoline and natural gas, hydrogen is flammable and can behave dangerously under specific conditions. Hydrogen can be handled safely when simple guidelines are observed and the user has an understanding of its behavior. The following lists some of the most notable differences:

1) Hydrogen is lighter than air and diffuses rapidly. Hydrogen has a rapid diffusivity (3.8 times faster than natural gas), which means that when released, it dilutes quickly into a non-flammable concentration. Hydrogen rises 2 times faster than helium and 6 times faster than natural gas at a speed of almost 45 mph (20 m/s). Therefore, unless a roof, a poorly ventilated room or some other structure contains the rising gas, the laws of physics prevent hydrogen from lingering near a leak (or near people using hydrogen-fueled equipment). Simply stated, to become a fire hazard, hydrogen must first be confined—but as the lightest element in the universe, confining hydrogen is very difficult. Industry takes these properties into account when designing structures where hydrogen will be used. The designs help hydrogen escape up and away from the user in case of an unexpected release.

2) Hydrogen is odorless, colorless and tasteless, so most human senses won't help to detect a leak. However, given hydrogen's tendency to rise quickly, a hydrogen leak indoors would briefly collect on the ceiling and eventually move towards the corners and away from where any nose might detect it. For that and other reasons, industry often uses hydrogen sensors to help detect hydrogen leaks and has maintained a high safety record using them for decades. By comparison, natural gas is also odorless, colorless and tasteless, but industry adds a sulfur-containing odorant, called mercaptan, to make it detectable by people. Currently, all known odorants contaminate fuel cells (a popular application for hydrogen). Researchers are investigating other methods that might be used for hydrogen detection: tracers, new odorant technology, advanced sensors and others.

3) Hydrogen flames have low radiant heat. Hydrogen combustion primarily produces heat and water. Due to the absence of carbon and the presence of heat-absorbing water vapor created when hydrogen burns, a hydrogen fire has significantly less radiant heat compared to a hydrocarbon fire. Since the flame emits low levels of heat near the flame (the flame itself is just as hot), the risk of secondary fires is lower.

4) Like any flammable fuel, hydrogen can combust. But hydrogen's buoyancy, diffusivity and small molecular size make it difficult to contain and create a combustible situation. In order for a hydrogen fire to occur, an adequate concentration of hydrogen, the presence of an ignition source and the right amount of oxidizer (like oxygen) must be present at the same time. Hydrogen has a wide flammability range (4-74% in air).

Meanwhile, plants require hydrogen to form carbohydrates and sugars. Plants currently assemble all of their hydrogen requirements by splitting water molecules $H_2O$ in the photosynthetic process in the leaves of plants when exposed to sunlight. So hydrogen is already present in the leaves and is a molecule synthesized for plant growth.

Existing technology in this field is believed to have significant limitations and shortcomings. For this reason and those described above, a need exists for the present invention.

All US patents and patent applications, and all other published documents mentioned anywhere in this application are incorporated by reference in their entirety.

BRIEF SUMMARY OF THE INVENTION

The invention provides systems and methods which are practical, reliable and efficient, and which are believed to fulfill the need and to constitute an improvement over the background technology, The invention has at least the following aspects:

1. A system including a compression source, reagent source, and grid of tubes in a field of crops, to prescriptively distribute an air pollution negating reagent into the atmosphere immersing the a field of crops.
2. Introduction of a reagent that is non-toxic to plants, over a large acreage, wherein said reagent induces an oxidation-reduction chemical reaction with the air pollution present throughout the acreage of crops, by means of the reaction effectually neutralizing the harmful effects of the air pollutants notably $O_3$ and $NO_x$ on the crops.
3. Said reagent is hydrogen $H_2$ gas that is delivered in the distribution grid at a diluted ratio not to exceed the flammability point of 4% $H_2$ concentration in ambient air.
4. The delivering actuation and rate of delivery of the reagent is determined by the level of air pollution, so that the chemical reaction neutralizing effect envelopes, but does not vastly exceed the space occupied by the crops' foliar canopy.
5. Hydrogen delivery in aerial application as an airborne fertilizer to stimulate carbohydrate formation in the leaves of plants.
6. Source of reagent is a compressed tank.
7. Source of reagent is a steam methane reformer.
8. Source of reagent is electrolysis.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 illustrates an embodiment of the present invention.

DETAILED DESCRIPTION

The present invention provides a Crop Growth Enhancement Method using a Reagent to Neutralize Air Pollutants. $O_3$ ozone, nitric oxide and nitrogen dioxide are common oxidation agents associated with air pollution and are very deleterious to human health and plant/crop health and productivity. Ozone in particular is a problem with respect to air pollution, human health and plant health. Ozone is very chemically reactive and is known in the chemical sciences as a free radical.

An oxidizing agent transfers oxygen atoms to a substrate. In this context, the oxidizing agent can be called an oxygenation reagent or oxygen-atom transfer (OAT) agent.

The present invention relates to introducing a reducing chemical reagent and oxygen molecule acceptor of an oxidation-reduction reaction. In the case of Hydrogen gas being the acceptor the reaction is either:

$O_3+H_2 \rightarrow O_2+H_2O$ for ozone as oxidizing agent or $2NO+2H_2 \rightarrow N_2+2H_2O$ for nitric oxide as oxidizing agent or $2NO_2+4H \rightarrow N+4H_2O$ for nitrogen dioxide as oxidizing agent.

Because hydrogen gas is a very active reducing agent with the oxidizing agent $O_2$, hydrogen is highly explosive in air. However, in prescriptive amounts where the concentration of the $H_2$ gas in ambient air is less than 4% (below combustion point), the hydrogen is not flammable or explosive.

The flammability limits based on the volume percent of hydrogen in air at 14.7 psia (1 atm, 101 kPa) are 4.0 and 75.0. The flammability limits based on the volume percent of hydrogen in oxygen at 14.7 psia (1 atm, 101 kPa) are 4.0 and 94.0.

The limits of detonability of hydrogen in air are 18.3 to 59 percent by volume

The present invention is a system with a hydrogen source, a compressor, and manifolds lines to distribute $H_2$ or other $O_3$ neutralizing agent based upon pollution levels.

Source of hydrogen is preferably a semi-portable tank

Source of hydrogen is a steam methane reformer

Reagent gas reacts with the Ozone gas within the system (reacts with and neutralizes ozone) and then enough reagent is left to react and neutralize Ozone in the leafy plant canopy.

Sensors are employed to a controller to prescriptively add $H_2$ at a rate sufficient to normalize the $O_3$ levels present in the leafy area of the crops. The hydrogen diffuses rapidly from the emitters and is lighter than air so rises up through the plant canopy into the surrounding air.

The systems seeks to achieve a special prescription of 0.097 ppm which is the ozone level in Fresno, Calif., one of the most polluted regions of the United States. Similar high pollutant levels are present through San Joaquin Valley, the region which produces most of the fruits, nuts and vegetables consumed in the US.

While applications of reagent may take place 24/7, in the preferred embodiment the prescription rate is higher and matches the higher pollution levels associated with photochemical reaction during high sunlight, at which time the plants' stomata are at their most open state therein allowing the toxic $O_3$ gas to enter the interior leaf space where damage occurs from the air pollutants, and/or, rate of delivery can be adjusted to the dynamic ambient $O_3$ by employing a real-time air pollutant metering device positioned in the leafy plant canopy.

The current inventor has spent years developing $CO_2$ gaseous delivery systems to open field crops. It is well known in the sciences that air pollution is deleterious to crop yields especially in regions synonymous with nasty air pollution like Central Valley California, China, Mexico, Brazil and other regions around the globe. Two primary air pollutants that are toxic to crops and suppress production are $NO_x$ and the resulting photochemical smog ozone $O_3$. In Fresno Calif., the highest air pollution in the US, $O_3$ levels are at 0.097 PPM.

The present invention uses compressors, manifolds, and tubes/tapes with emitters to introduce prescriptive levels of hydrogen gas, aerosol hydrogen peroxide or other reactive gases or aerosols that are not harmful to crops, but that will react and neutralize the $O_3$ ozone and react with the $NO_x$ to neutralize it and prevent the formation of photochemical ozone immediately adjacent and surrounding the crops' leafy canopy.

In the first step 12 of the method, hydrogen is acquired from one of several sources, including: electrolysis of water or other hydrogen-containing substance, delivered in pure form in tanks, harvested from methane or other hydrocarbon using steam reforming, or another source.

The hydrogen gas is filtered of impurities in the second step 14 of the method using a hydrogen purification device. This step may not be necessary in the case of tank delivered hydrogen, but is necessary for hydrogen sourced from hydrocarbons such as methane. Possible hydrogen purification methods include palladium membranes, dense thin-metal membrane purifiers, pressure swing adsorption, catalytic recombination, or an electrochemical purification system, the latter of which can have the added benefit of compressing the hydrogen simultaneously.

The third step 16 is the compression of the purified hydrogen for ease of storage. Possible methods for compressing hydrogen include: reciprocating piston compressors, ionic liquid piston compressors, hydride compressors, piston-metal diaphragm compressors, guided rotor compressors, and the highly efficient electrochemical hydrogen compressor. The compressed hydrogen can then be stored in containers until needed or be directed into the system immediately.

In the fourth step 18, the hydrogen is diluted with ambient air or other gaseous media so that the hydrogen component is equal to, or less than, 4% of the total gaseous mixture, which will prevent the hydrogen from sustaining a spontaneous combustive reaction, should an ignition source be present. This dilution is preferably accomplished using a venturi valve 19. The venturi valve dilution process utilizes the Venturi effect, whereby a constriction of the diameter for a short stretch of the valve causes a drop in pressure. The low pressure area creates suction which draws in a diluent such as oxygen which mixes with the hydrogen gas stream.

During the fifth step 20 of the method the pressure is modified as needed by a pressure regulator 21, and the flow rate is regulated by a flow control valve 22. The regulator 21 can be a single-stage or double-stage regulator. The flow control valve 22 is preferably connected via a layflat manifold 24 to the array of piping which distributes gas throughout the crop field.

The layflat manifold 24 is commonly used by growers to deliver water. Using a layflat manifold to deliver gas therefore has the advantages that those managing the field are familiar with its service and maintenance. The flow rate of the valve 22 is set so that just enough hydrogen is introduced so that the ongoing chemical reaction occupies the leafy crop canopy and immediately adjacent area. The release point 25 of the reagent is preferably just below the leafy canopy of the crop. For certain crops that do not benefit from direct exposure to a reagent such as hydrogen, the release point would then be directly above the leafy canopy. In this case the diluted hydrogen would not contact the crops as hydrogen rises above the air. The hydrogen then neutralizes the existing $NO_x$ and ozone in the local sphere. Furthermore, new $NO_x$ and $O_3$ that is moving into the leafy area by diffusion or dispersion across the chemical gradient created in the sphere by the initial neutralization is then neutralized.

Finally, the flow valve can be electronically adjusted by a reagent control unit 26. The reagent control unit 26 receives data from sensors 28A-D in the field. These sensors convey signals via wired or wireless means The types of sensors relaying data to the reagent control unit include: temperature sensors 28A, wind velocity anemometers 28B, photosynthetically active radiation level (PAR) sensors 28C, reagent concentration level sensors 28D, and pollutant concentration level sensors 28E. While the use of air quality sensors was expensive in the past, the 2010s saw a trend towards the development of cheaper air-quality sensors, making the final component of the system 10 affordable and beneficial.

The descriptions above and the accompanying materials should be interpreted in the illustrative and not the limited sense. While the invention has been disclosed in connection with the preferred embodiment or embodiments thereof, it should be understood that there may be other embodiments which fall within the scope of the invention.

The invention claimed is:

1. A method for enhancing plant crop growth, comprising the steps of:

a. providing a supply of H2 gas reagent;
b. filtering impurities from the reagent;
c. compressing the reagent;
d. storing the compressed reagent in a tank;
e. diluting the compressed reagent to below 4% concentration;
f. regulating the reagent pressure;
g. collecting data on temperature, photosynthetically active radiation levels (PAR), wind speed, pollutant concentration, and the reagent concentration within a canopy of the plant crop;
h. controlling a rate of flow of the compressed reagent using a valve connected to the tank, based on the data obtained; and
i. applying the reagent to the plant crop, whereby the reagent is used to neutralize air pollutants.

2. The method of claim 1, wherein a source of the reagent is electrolysis.

3. The method of claim 1, wherein a source of the reagent is a steam methane reformer.

4. The method of claim 1, wherein the filtration step is accomplished using an electrochemical purification system.

5. The method of claim 4, wherein the electrochemical purification system is communicatively connected to a reagent source via a hose.

6. The method of claim 1, wherein the step of compressing the reagent is accomplished by an electrochemical hydrogen compressor.

7. The method of claim 6, wherein the electrochemical hydrogen compressor is communicatively connected to a filtration device via a hose.

8. The method of claim 7, wherein the reagent storage tank is communicatively connected to the electrochemical hydrogen compressor via a hose.

9. The method of claim 1, wherein the reagent is diluted using a venturi valve.

10. The method of claim 9, wherein the venturi valve is communicatively coupled to the tank via a hose.

11. The method of claim 1, wherein the step of regulating reagent pressure is accomplished by a regulator communicatively coupled to a dilution mechanism via a hose.

12. The method of claim 11, wherein the pressure regulator is a single-stage or double-stage regulator.

13. The method of claim 11, wherein the flow control valve is communicatively coupled to a piping distribution array via a lay flat manifold and which is communicatively coupled to the pressure regulator via a hose.

14. The method of claim 1, wherein the step of regulating reagent pressure is accomplished by a control unit communicatively coupled to the flow control valve and sensors, communicatively connected to the control unit, embedded in the field.

15. The method of claim 1, wherein a rate of application of the reagent is determined by the level of air pollution, so that a chemical neutralizing effect envelopes, but does not exceed, the space occupied by the crops' canopy.

* * * * *